United States Patent

Tai et al.

Patent Number: 4,990,694
Date of Patent: Feb. 5, 1991

[54] OPTICALLY ACTIVE DIMETHYL HEPTANEDIOLS

[75] Inventors: Akira Tai, Minoo; Takashi Sugimura, Himeji, both of Japan

[73] Assignee: Wako Pure Chemical Industries Ltd., Osaka, Japan

[21] Appl. No.: 482,928

[22] Filed: Feb. 22, 1990

[30] Foreign Application Priority Data

Feb. 27, 1989 [JP] Japan .................. 64-46293

[51] Int. Cl.$^5$ ............................................. C07C 31/20
[52] U.S. Cl. .................................................. 568/852
[58] Field of Search ......................................... 568/852

[56] References Cited

FOREIGN PATENT DOCUMENTS

| 158733 | 9/1982 | Japan | 568/852 |
| 32727 | 2/1985 | Japan | 568/852 |
| 186840 | 8/1985 | Japan | 568/852 |

Primary Examiner—J. E. Evans
Attorney, Agent, or Firm—Donald W. Hanson

[57] ABSTRACT

(3S, 5S)-(−)-2,6-dimethyl-3,5-heptanediol expressed by the following formula:

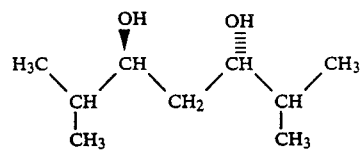

and (3R, 5R)-(+)-2,6-dimethyl-3,5-heptanediol expressed by the following formula:

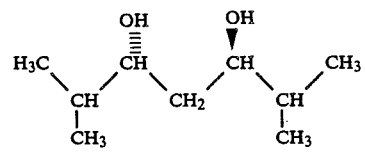

are disclosed, which are useful as reagents for asymmetric synthesis such as chiral auxiliary and chiral synthon.

2 Claims, No Drawings

OPTICALLY ACTIVE DIMETHYL HEPTANEDIOLS

BACKGROUND OF THE INVENTION

This invention relates to novel optically active compounds useful as reagents for asymmetric synthesis such as chiral auxiliaries and chiralsynthon.

An optically active diol is very useful as a reagent for various asymmetric synthesis such as asymmetric source in the synthesis of optically active acetal or chiral auxiliary in a diastereo-differentiating Simmons-Smith reaction. The most representative compound among optically active diols heretofore used as a reagent for asymmetric synthesis is 2,4-pentanediol (hereinafter referred to as PD). Optically active PD, however, has a comparatively low melting point of 50.5° C. In addition, it has very high moisture absorption property and can be hardly dried. Therefore, it is difficult to handle. Further, it possesses problems particularly when it is used for an anhydrous reaction. Accordingly, a novel optically active diol has been desired which is free from the above problems and has excellent properties as a reagent for asymmetric synthesis.

SUMMARY OF THE INVENTION

An object of the invention is to provide a novel optically active diol which has excellent properties as a reagent for asymmetric synthesis, has very high melting point compared to optically active PD, is free from a moisture absorption property and hence capable of ready handling and further can be used for anhydrous reactions.

The above and other objects, features and advantages of the invention will become more apparent from the following description.

DETAILED DESCRIPTION OF THE INVENTION

According to the invention, there is provided (3S, 5S)-(−)-2,6[1-dimethyl-3,5-heptanediol (hereinafter abbrebiated as (3S, 5S)-(−)-DMHD) expressed as

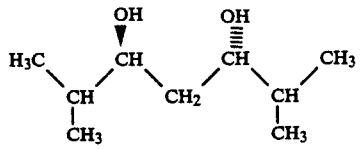

According to the invention, there is also provided (3R, 5R)-(+)-2,6-dimethyl-3,5-heptanediol (hereinafter abbreviated as (3R, 5R)-(+)-DMHD) expressed as

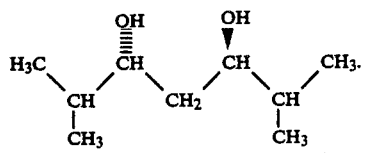

The compounds according to the invention can be readily synthesized in a enantio-differentiating hydrogenation reaction of 2,6-dimethyl-3,5-heptanedione, for instance.

More specifically, for obtaining (3S, 5S)-(−)-DMHD, 2,6-dimethyl-3,5-heptanedione is charged together with an adequate organic solvent (e.g., tetrahydrofuran (THF), methyl propionate, ehtyl acetate, etc.) and a small amount of acetic acid (or pivalonic acid or propionic acid) into an autoclave. Further, Raney Ni ((R, R)-tartaric acid-NaBr-RNi) modified by a mixture of (R, R)-tartaric acid and NaBr is added, and then hydrogen is introduced. The system is then shaken or agitated for reaction under conditions of 80 to 120 kg/cm$^2$ and 80 to 120° C., preferably 90 to 100° C., for 2 to 10 days. After the reaction, the system is cooled down to cause evacuation of hydrogen. The system is then filtered to remove insolubles, and then solvent is distilled off from the filtrate. In this way, a colorless solid is obtained quantitatively. This solid is subjected to recrystallization one to several times in the usual way using an adequate organic solvent (e.g., diethylether, diisopropylether, etc.). As a result, (3S, 5S)-(−)-DMHD which is free from racemic modification is obtained in the form of colorless needle-like crystals.

By using (S, S)-tartaric acid-NaBr-RNi in lieu of (R, R)-tartaric acid-NaBr-RNi, (3R, 5R)-(+)-DMHD can be obtained instead of (3S, 5S)-(−)-DMHD.

2,6-dimethyl-3,5-heptanedione which is used as starting material may be readily obtained through Claisen condensation of methyl isobutyrate and methylisopropyl ketone which is brought about in a manner as disclosed, for instance, in J. Am. Chem. Soc., 66, 1220 (1944).

(R, R)- or (S, S)- tartaric acid-NaBr-RNi may be readily prepared by- dipping Raney Ni catalyst in a modifying solution consisting of (R, R)- or (S, S)- tartaric acid and NaBr at 60° to 100° C. for ten minutes to several hours in a manner as disclosed in Chem. Lett. 1978, 1195.

The compounds according to the invention can of course be synthesized by other methods than those described above, for instance through asymmetric reduction of 2,6-dimethyl-3,5-heptanedione using BINAP (2,2'-bis(diphenylphosphino)-1,1'-dinaphthyl)-Ru (II) complex as a catalyst.

Regarding 2,6-dimethyl-3,5-heptanediol, racemic and meso modifications are well-known and disclosed in various literatures. However, optically active 2,6-dimethyl-3,5-heptanediol, i.e., (3S, 5S)-(−)-DMHD and (3R, 5R)-(+)-DMHD, has never been specifically disclosed in any literature. Thus, the compounds according to the invention are first synthesized and their nature is confirmed by the present inventors, and they are novel compounds unseen in any literature.

The compounds according to the invention have a high melting point of 92° C., in comparison with the melting point of optically active PD which is 50.5° C., slightly higher than room temperature. In addition, while optically active PD has a very high moisture absorption property and can be hardly dried, the subject compounds are in the form of needle-like crystals and free from a moisture absorption property and capable of ready handling. Therefore, far superior properties to that of optically active PD can be obtained in quantitative use for anhydrous reactions. Further, the compounds according to the invention can be recovered by the usual extraction operations because of their high fat-solubility unlike optically active PD. For instance, when optically active PD is extracted with organic solvents such as benzene, diethylether etc., PD remains in the water layer, but with the compounds according to the invention more than 95 % is shifted to the oil layer. This is one of the features of the invention.

When the compounds according to the invention are used as chiral auxiliary in diastereo-differentiating Simmons-Smith reaction of cyclohexane derivatives, the asymmetric yield is obviously improved to be 99.8 % max or above compared to an asymmetric yield of 95 % max in case when optically active PD is used as the chiral auxiliary. Besides, while, in the case of the use of optically active PD, the selectivity is extremely influenced by conditions of reaction such as solvent and temperature, with the compounds according to the invention these conditions of reaction are very slightly influential.

With the compound according to the invention, i.e., R=iso C$_3$H$_7$, used as asymmetric source for the following reaction the selectivity is extremely improved to be 799 : 1 in comparison with the fact that in the case of use of optically active PD (R=CH$_3$) as asymmetric source the diastereo ratio of the product [X] is 87:13 (Tetrahedron Lett., 25, 3947-3950 (1984)).

It is well known that optically active alcohol can be readily obtained by oxidizing the product [X] in the usual way and treating it with a base.

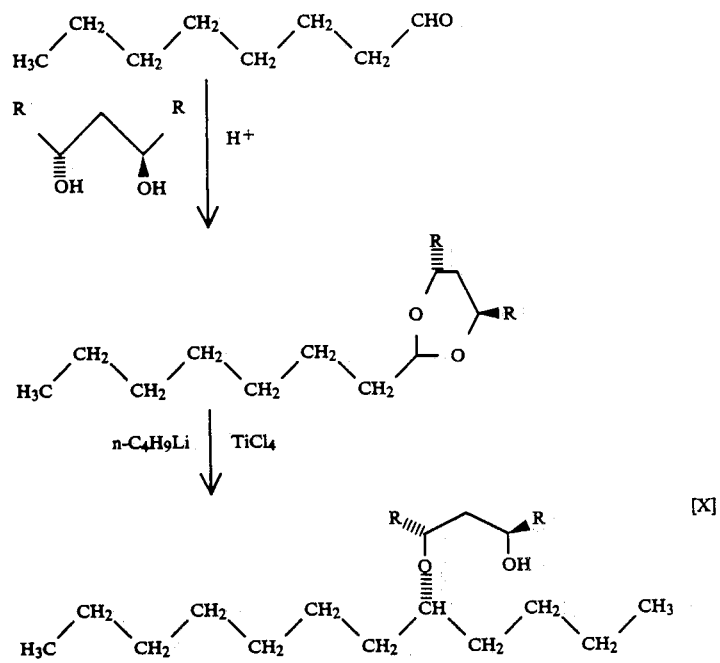

As is shown, the compound according to the invention is very promising for use as chiral auxiliary for the improvement of reaction using optically active PD or as chiral synthon or the like of reaction incapable of use of optically active PD. Further, compounds incorporating the compound according to the invention show chemical behavior roughly equivalent to that of compounds incorporating optically active PD. Thus, the compounds according to the invention can be used in the case of various well-known asymmetric synthesis using optically active PD as in the case of optically active PD. By this fact, the usefulness of the compounds of this invention is also recognized.

Now, examples and reference examples will be given without any sense of limiting the invention.

Reference example 1 Synthesis of 2,6-dimethyl-3,5-heptanedione

In a nitrogen stream, 83 g of sodium amide was added to 1 l of dry diethylether, and while agitating the resultant system, a solution containing 180 ml of dry diethylether and 183 g of 3-methyl-2-buthanone was dropped into the system by taking 10 minutes. Subsequently, after agitating the system for 5 minutes, a solution containing 180 ml of dry diethylether and 217 g of methyl isobutyrate was added to the system. The resultant system was further agitated for 2 hours. After the reaction, the reaction liquid was neutralized with N-HCl, and the product was extracted by adding 1 l of water and 1 l of diethylether. Ether layer was then concentrated. The resultant residue was refined by repeatedly carrying out distillation, thus obtaining 110 g of 2,6-dimethyl-3,5-heptanedione. The yield was 33.1 %, and b.p. was 85°-87° C./35 mm Hg.

Reference example 2

Preparation of (R, R)-tartaric acid-NaBr-RNi (1) Preparation of modifying solution 20 g of (R, R)-(+)-tartaric acid and 200 g of NaBr were dissolved in 2 l of deionized water, and the pH of the solution was adjusted with N—NaOH to 3.2.

(2) Preparation of Raney Ni catalyst 90 g of NaOH was dissolved in 400 ml of deionized water, and 38 g of sufficiently pulverized Raney nickel alloy (Ni:Al=42:58) was added in small quantities to the solution by taking 15 minutes. The resultant suspension was held at 100° C. for one hour. Then, aqueous solution of alkali was removed by decantation, and the catalyst was washed 15 times with 500 ml of deionized water.

(3) Preparation of (R, R)-tartaric acid-NaBr-RNi 16 g of Raney Ni catalyst obtained in (2) was dipped in the modifying solution obtained in (1) at 100° C. The system was held at the same temperature for one hour while occasionally shaking the container. Then the solution part was removed by decantation and the residue was washed with deionized water. After repeating this operation, the residue was washed with methanol and then with THF. In this way, the intended (R, R)-tartaric acid-NaBr-RNi was obtained.

Reference example 3: Preparation of (S, S)-tartaric acid-NaBr-RNi

Reactions were carried out in the same way as in Reference example 2 except for that (S S)-(−)-tartaric acid was used in lieu of (R, R)-(+)-tartaric acid to obtain (S, S)-tartaric acid-NaBr-RNi.

EXAMPLE 1

Synthesis of (3S, 5S)-(−) DMHD 102 g of 2,6-dimethyl-3,5-heptanedione obtained in Reference example 1, 220 ml of THF and 2 ml of acetic acid were charged into an autoclave. Then, (R, R)-tartaric acid-NaBr-RNi obtained in Reference example 2 (prepared by using 38 g of Raney nickel alloy) was added. Then hydrogen was introduced to adjust the inner pressure to 100 kg/cm². In this state, the system was shaken for reaction for one week by holding ah inner temperature of 100° C. After the reaction, the system was cooled down, and hydrogen was evacuated. The content in the autoclave was then taken out, and its insoluble materials were filtered out. The filtrate was concentrated to obtain a colorless solid, which was subjected to re-crystallization three times using 200 ml of diethylether. As a result, 31.4 g of (3S, 5S)-(−) DMHD was obtained in the form of colorless needle-like crystals. The yield was 30.0 %, m.p. 91.5°-92° C.

[α]$_D$= −63.8° (C=1.0, CH$_3$OH)

Optical purity : 99% ↑ (based on HPLC analysis)
Elemental analysis value : C$_9$H$_{20}$O$_2$=160.26
Analytical value : C ; 67.01, H : 12.59
Theoretical value : C ; 67.45, H ; 12.58.

$^1$H-NMR (CDCl$_3$) : δppm : 3.66–3.62 (m, 2H, CH-OH), 2.12 (d, J=4.4Hz, 2H, OH), 1.71 (dh, J=6.8Hz, 2H,

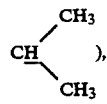

), 1.61–1.59 (m, 2H, CH$_2$), 0.96 (d, J=6.8Hz, 6H, CH$_3$), 0.91 (d, J=6.8Hz, 6H, CH$_3$).

IR (neat) : 3360cm$^{-1}$ (OH), 2980cm$^{-1}$, 2920cm$^{-1}$, 1401 cm$^{-1}$, 1390 cm$^{-1}$, 1040 cm$^{-1}$.

The absolute configuration of this compound was determined to be (3S, 5S) because of the coincidence of the direction of optical rotation of a compound A ([α]$_D$= −50.4°), which was obtained by partial oxidization of this compound, and that of a compound [A] derived from (S)-(−)-[B] having a well-known absolute configuration.

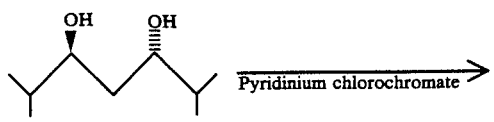

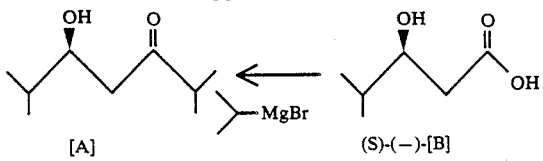

EXAMPLE 2

Synthesis of (3R, 5R)-(+)-DMHD

Reaction and after-treatment were carried out in the same way as in Example 1 except for that (S, S)-tartaric acid-NaBr-RNi was used in lieu of (R, R)-tartaric acid-NaBr-RNi to obtain 30.8 g of (3R, 5R)-(+)-DMHD in the form of colorless needle-like crystals. The yield was 29.4 %.

m.p. 91.5°-92° C.
[α]$_D$=63.2° (C=1.0, CH$_3$OH)

Optical purity: 99 % (based on HPLC analysis) $^1$H-NMR and IR were the same compounds as obtained in Example 1. Application Example 1: Diastereo-differentiating Simmons-Smith reaction of cyclohexene derivative

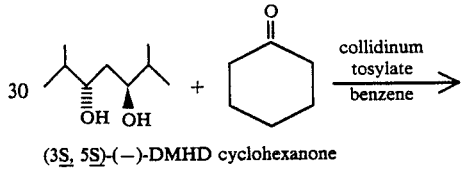

(3S, 5S)-(−)-DMHD cyclohexanone

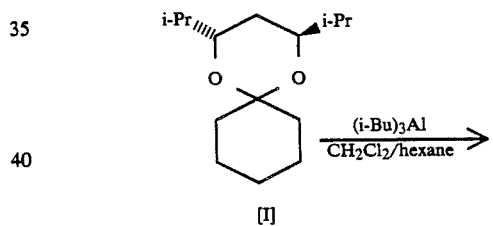

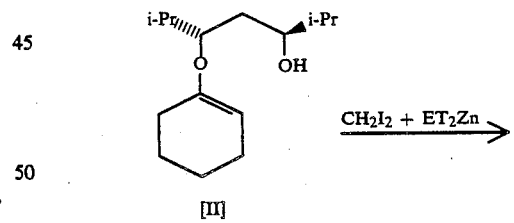

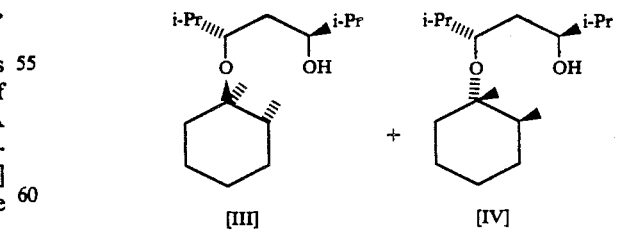

Compound [II] was obtained by carrying out the reaction of compound [I], which was obtained through reflux reaction of (3S, 5S)-(−)-DMHD and cyclohexanone in benzene in the presence of collidinum tosylate (yield being 87 %), with triisobutyl aluminum in CH$_2$Cl$_2$/hexane at 0° C. and followed by the after-treatment the reaction product with NaOH solution (yield being 98 %).

333 mg of this compound [II] was dissolved in 10 ml of a solvent shown in Table 1, 7 ml of 1 M hexane solution of diethyl zinc was added at a temperature shown in Table 1, and then was added methylene iodide dropwise at the same temperature. The reaction mixture was agitated for a constant period of time as shown in Table 1. After the reaction, a saturated aqueous solution of ammonium chloride was added to the resultant and it was cooled, and the product was extracted with diethylether. The extracted solution was concentrated and refined by medium pressure chromatography (MPCL) using silica gel to obtain 304 mg of diastereomer mixture ([III]+[IV]). The result is shown in Table 1. The mixture ratio of diastereomer was analyzed and determined using $^{13}$C-NMR and capillary GLC. It was confirmed that what was greatly led to (1S, 6S)-(−)-1-bicyclo[4.1.0] heptanol was the compound [III].

TABLE 1

| No. | solvent | reaction temperature | reaction time (hr) | yield (%) | diastereomer exess (%) |
|---|---|---|---|---|---|
| 1 | hexane | 0 | 1.5 | 54.3 | 98.8 |
| 2 | hexane | −40 to 0 | 2.5* | 75.3 | 98.8 |
| 3 | diethylether | 20 | 1.5 | 86.4 | 99.8 |
| 4 | diethylether | 0 | 3 | 72.0 | 99.4 |
| 5 | diethylether | −40 | 27 | 59.3 | 95.0 |
| 6 | tetrahydrofuran | 20 | 2.5 | 69.0 | 95.8 |

*After reaction at −40° C. for 0.5 hour, the temperature was raised to 0° C. in 1.5 hours, and then reaction was carried out at 0° C. for 0.5 hour.

REFERENCE EXAMPLE 4

Cyclohexene derivative was synthesized in the same way as in Application example 1 except for that (S, S)-(−)-PD was used in lieu of (3S, 5S)-(−)-DMHD, and diastereo-differentiating Simmons-Smith reaction was performed in the same way as in Example 1. The result is shown in Table 2.

TABLE 2

| No. | solvent | reaction temperature | reaction time (hr) | yield (%) | diastereomer exess (%) |
|---|---|---|---|---|---|
| 1 | hexane | 0 | 6 | 51.8 | 40.8 |
| 2 | benzene | 20 | 2.5 | 67.9 | 49.2 |
| 3 | dichloromethane | 0 | 1.5 | 72.7 | 14.2 |
| 4 | diisopropylether | 0 | 2 | 77.3 | 56.8 |
| 5 | diethylether | 0 | 4 | 72.5 | −7.8 |
| 6 | dioxane | 20 | 14 | 58.8 | 92.0 |
| 7 | tetrahydrofuran | 20 | 20 | 64.7 | 93.6 |
| 8 | dimethoxyethane | 20 | 14 | 55.7 | 95.2 |

As is obvious from Tables 1 and 2, in the case of the diastereo-differentiating Simmons-Smith reaction based on optically active PD, the diastereomer exess (d.e.) varies greatly depending on the kind of solvent and reaction temperature, and d.e. is only about 95 % even in the best case (i.e., in case of dimethoxyethane solvent).

In the case of the diastereo differentiating Simmons-Smith reaction based on the compound according to the invention, d.e. is above 95 % irrespective of the kind of solvent and reaction temperature. Particularly, in the case of diethylether solvent and reaction temperature of 20° C., d.e. is 99.8 % or above, indicating that it is possible to obtain a compound substantially free from compound [IV].

Further, it is seen that the chemical yield is higher in general in the case of the Simmons-Smith reaction based on the compound according to the invention than in the case of the Simmons-Smith reaction based on optically active PD.

Application examples 2 to 6

Diastereo-differentiating Simmons-Smith reaction (diethyl ether solvent, 20° C., 1.5 hr.) was carried out in the same way as in Application example 1 except for that cyclopentanone, cycloheptanone, cyclooctanone, 4,4-dimethylcyclohexanone and 3-pentanone were used in lieu of cyclohexanone. In either case the diastereomer exess (d.e.) was 99 % or above, and the yield was as high as 85 to 95 %.

As has been described in the foregoing, according to the invention there is provided a novel optically active diol, which has a far higher melting point than that of optically active PD, does not absorb moisture, can be readily handled and can be used for anhydrous reactions. When the compound according to the invention is used as reagent for asymmetric synthesis (1) it is possible to obtain high stereo selectivity compared to the case of use of optically active PD, and (2) the selectivity is hardly influenced by such reaction conditions as the kind of solvent and reaction temperature. With these effects, the compound according to the invention is promising for use as chiral auxiliary for the synthesis of various physiologically active compounds, e.g., improvement of reactions using optically active PD or as chiral synthon of reaction for which PD could not have been used.

We claim:

1. (3S, 5S)-(−)-2,6-dimethyl-3,5-heptanediol expressed by the following formula:

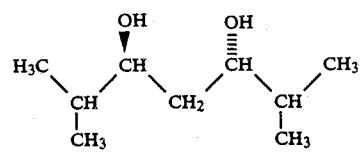

2. (3R, 5R)-(+)-2,6-dimethyl-3,5-heptanediol expressed by the following formula:

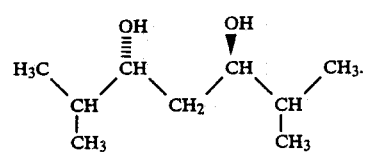

* * * * *